United States Patent [19]
El Khoury

[11] Patent Number: 6,011,022
[45] Date of Patent: Jan. 4, 2000

[54] TOPICAL APPLICATION OF MUSCARINIC ANALGESIC DRUGS SUCH AS NEOSTIGMINE

[76] Inventor: George F. El Khoury, 1561 Ramillo Ave., Long Beach, Calif. 90815

[21] Appl. No.: 09/083,431

[22] Filed: May 21, 1998

Related U.S. Application Data

[60] Provisional application No. 60/076,582, Mar. 3, 1998.
[51] Int. Cl.$^7$ ..................................................... A61K 31/66
[52] U.S. Cl. .......................... 514/78; 514/946; 514/969; 514/940; 514/947
[58] Field of Search ............................. 514/78, 946, 969, 514/940, 947

[56] References Cited

U.S. PATENT DOCUMENTS

| | | | |
|---|---|---|---|
| 3,275,510 | 9/1966 | Magid et al. | 514/946 |
| 4,328,222 | 5/1982 | Schmidt | 424/244 |
| 4,416,886 | 11/1983 | Bernstein | 424/260 |
| 4,626,539 | 12/1986 | Aungst et al. | 514/282 |
| 4,783,450 | 11/1988 | Fawzi et al. | 514/78 |
| 4,871,750 | 10/1989 | Roberts | 514/328 |
| 4,897,260 | 1/1990 | Ross et al. | 424/59 |
| 5,069,909 | 12/1991 | Sharma et al. | 424/499 |
| 5,589,480 | 12/1996 | Elkhoury et al. | 514/282 |
| 5,654,337 | 8/1997 | Roentsch et al. | 514/570 |
| 5,725,871 | 3/1998 | Illum | 424/434 |

FOREIGN PATENT DOCUMENTS

WO 9213540  8/1992  WIPO.

OTHER PUBLICATIONS

J. L. Joris et al., *Anesth. Analog.,* Opioid Analgesia At Perhipheral Sites: A Target for Opioids Released During Stress and Inflammation? 66:1277–81 (1987).
H. Bouaziz. MD et al., *Anesth Analg.,* "Postoperative Analgesia from Intrathecal Neostigmine in Sheep," 80:1140–4 (1995).
G. Lauretti, MD et al., *Anesth Analg.,* "Dose–Response Study of Introthecal Morphine Versus Intrathecal Neostigmine, Their Combination . . . " 82:1182–7 (1996).
S. Abram, MD et al., *Anesth Analg.,* "Intrathecal Acetyl Cholinestrerase Inhibitors Produce Analgesia That is Synergistic with Morphine and Clonidine in Rats," 81:501–7 (1995).
C. Stein , M.D. et al., *New England Journal of Medicine,* vol. 325, No. 16 "Analgesic Effect of Intraarticular Morphine After Arthroscopic Knee Surgery," pp. 1123–1126, (1991).

T. Yaksh, Ph.D. et al.,*Anesthesiology,* "Studies on the Safety of Chronically Administered Intrathecal Neostigmine Methylsulfate in Rats and Dogs," V 82. No.2, Feb. 1995.
"Morphine —A Local Analgesic," International Association for the Study of Pain, vol. III, (1995).
G. Lauretti, MD et al., *Anesth Analg* "The Effects of Intrathecal Neostigmine on Somatic and Visceral Pain: Improvement by Associate with a Peripheral Anticholinergic," 81:615–20 (1996).
D. Hood, M.D., et al., *Anesthesiology,* "Phase I Safety Assessment of Intrathecal Neostigmine Methylsulfate in Humans," V 82., No. 2, Feb. 1995 pp. 331–342.
Goodman & Gillman's, *The Pharmacological Basis of Therapeutics,* 9th Ed., McGraw–Hill pp. 141–175, (1987).
Tennant et al. Abs. of Int. Pharm. Abs. (Lancet) v. 342 (Oct. 23, 1993) pp. 1047–1048.
Letters to the Editor, *The Lancet,* vol. 342, Oct. 23, 1993, pp. 1047–1048.
C, Stein, M.D., "The Control of Pain in peripheral Tissue by Opioids," *Mechanisms of Disease,* vol. 332, No. 25, pp. 1685–1690, (1995).
C. Williams, Intrasite Gel: A Hyrogel Dressing, Product Focus (3–page article) (1995).
Remington Pharmaceutical Sciences 18th ed., Chapter 87, "Medicated Applications," pp. 1596–1614 (1990).
C. Stein, "Peripheral and Non–Neuronal Opioid Effects," *Current Scient Ltd.,* 1–85922–136–X ISSN 0952–7907, pp. 347–351 (1991).
S. Moiniche, et al., "Peripheral Antinociceptive Effects of Morphine After Burn Injury," *Acta Anaesthesiologica Scandinavica,* ISSN 0001–51772, pp. 710–712 (1993).
C. Stein, "Peripheral Mechanisms of Opioid Analgesia," *Anesth Analg 1993*; 76:182–92.
C. Stein et al., "Peripheral Opoid Receptors," *Annals of Medicine* 17:219–221 (1995).

*Primary Examiner*—James H. Reamer
*Attorney, Agent, or Firm*—Millen, White, Zelano, & Branigan, P.C.

[57] ABSTRACT

The invention is directed to methods and pharmaceutical compositions for the topical administration of analgesic drugs which affects peripheral muscarinic receptors such as neostigmine. In particular, the invention relates to topical administration of an analgesic agent, e.g., neostigmine, optionally in admixture with a skin- or mucosal-specific penetration enhancer, to produce a localized analgesic effect in inflamed or non-inflamed skin or mucosal tissue, and without a transdermal or transmucosal migration of the agent, e.g., into the central nervous system.

25 Claims, 1 Drawing Sheet

U.S. Patent    Jan. 4, 2000    6,011,022
FIG. 1
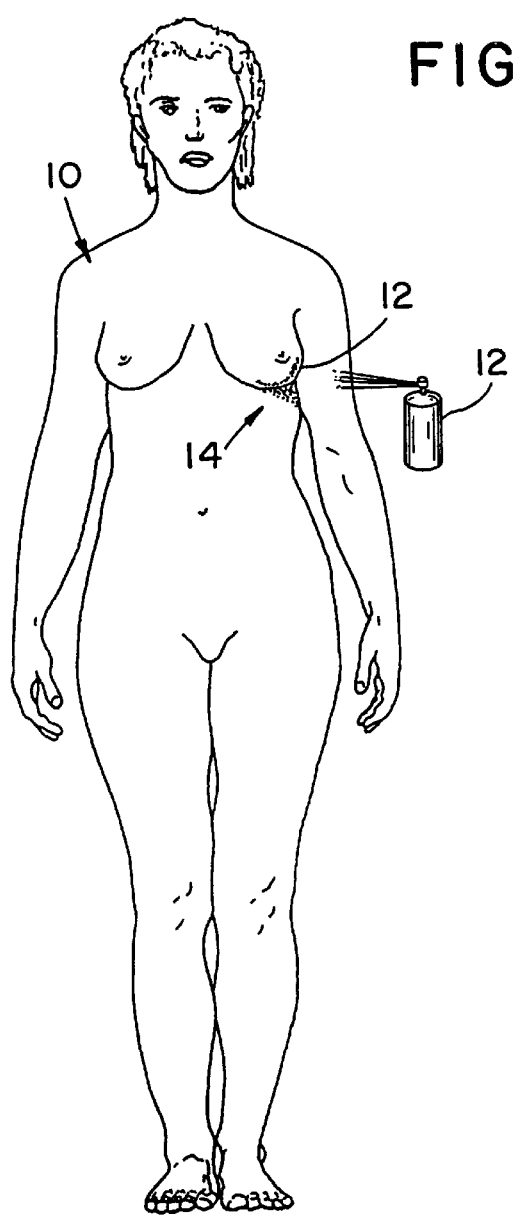
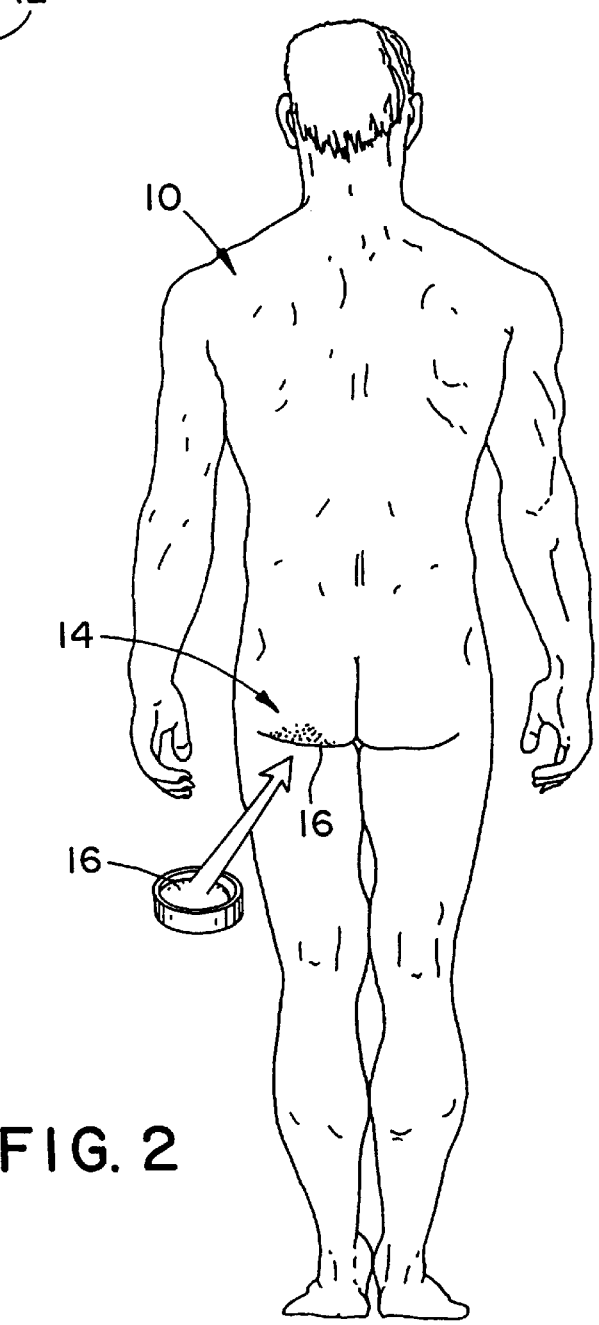
FIG. 2

TOPICAL APPLICATION OF MUSCARINIC ANALGESIC DRUGS SUCH AS NEOSTIGMINE

This application is a continuation of provisional appln No. 60/076,582, Mar. 3, 1998.

BACKGROUND OF THE INVENTION
Peripheral Opioid Analgesia

Morphine is the prototype of the class of opioid analgesic drugs which exert their effects by activating opioid receptors within the brain. When morphine is referred to individually in this application, this reference is meant to encompass other opioid drugs and is not meant to be morphine exclusively. Historically, narcotics have been used since the 18th century in the forms of oral or injectable morphine or opium in order to accomplish pain relief. Morphine is considered to be unsurpassed as an analgesic for severe pain.

Unfortunately, morphine and other opioid drugs have a number of severe side effects which hamper their wide spread use and acceptance by both physicians and patients. These side effects include: addiction, nausea, inhibition of breathing, somnolence and dysphoria, all of which are mediated by morphine's action within the brain. It is still the current belief that narcotics ingested or injected will cross to the blood stream and from there go to the brain where there are morphine receptors. At that time, the narcotics are believed to attach to these morphine receptors and create a dullness of the pain but with all of the side effects described above. Of course, the worst potential effect is the addiction that can occur if the morphine is used beyond a few days or weeks on a continuous basis.

Because of the fear of addiction, the use of morphine as an analgesic has been restricted. In addition, major research efforts have been directed toward the development of morphine-like drugs that act within the brain but are devoid of the side effects. The market for these other drugs has never fully materialized because these drugs were not perceived as having the same analgesic properties of morphine and because typically these drugs were not produced to be both available in oral and injectable formats.

In the past ten years, the intraspinal method of treating pain has been extensively developed but, as more extensive use was made of this technique, a number of serious problems developed. The first problem is that the intraspinal method of treatment requires a spinal tap which of course necessitates the use of a needle to the spinal cord. The second problem results from the first in that if it is necessary to use the intraspinal method over a period of time, such as two or three weeks, medication must be injected into the spine for this period of time and the continuous needle sticks into the spine has potential hazards. Further, if it is necessary to use the intraspinal method over time, even though the dosage is substantially less compared to oral or intravenous dosages, there is still a high potential for addiction and with such addiction the resultant problems of withdrawal and its associated side effects.

Although intraspinal application of narcotics is still used to alleviate pain after surgery, this technique has the limitations with the potential for addiction as described above. In addition, it has been determined that with frail patients there is the risk that the patient can stop breathing and there have been a number of cases of respiratory arrest after the administration of narcotics using the intraspinal technique. Further, the intraspinal technique of administering narcotics creates difficulty with male patients and especially with elderly male patients in that there can be problems with urination and with consequent problems of urine retention. Finally, this intraspinal technique produces a significant itching problem as a side effect.

In recent studies, it was discovered that opioid receptors may also be located in other peripheral tissues. This was reported in Stein, C. et al., Peripheral effect of fentanyl upon nociception in inflamed tissue of the rat. Neurosci. Lett. 84:225–228 (1988), and in Stein, C. et al., Antinociceptive effects of mu- and kappa-agonists in inflammation are enhanced by a peripheral opioid receptor-specific mechanism of action. Eur. J. Pharmacol. 155:255–264 (1988). Subsequently, animal experiments were performed in Dr. Stein's laboratory characterizing peripheral opioid receptors and their activation by morphine and other opioid drugs. Stein, C., et al., N. Engl. J. Med. 325:1123–1126 (1991) also reported the analgesic effect of intraarticular morphine after arthroscopic knee surgery. These results were reviewed in Stein, C., Peripheral mechanisms of opioid analgesia. Anesth. Analg. 76:182–191 (1993), and in Stein, C., Lehrgerger, K., Yassouridis, A., Khoury, G.: Opioids as novel intraarticular agents in arthritis. In: Progress in Pain Research and Management, Fields, H. L., Liebeskind, J. C., eds., 1:289–296, IASP Press, Seattle, (1994). A most important determination from these various studies is that the doses of the drugs required to produce analgesia in the peripheral tissues are extremely small and therefore devoid of the above mentioned side effects produced by dosages sufficient to operate on the brain.

In addition, it was determined that the endogenous ligands of peripheral opioid receptors (endorphins, the body's own pain killers) are located within the inflamed tissue. It was also determined that the endorphins can produce intrinsic analgesia within peripheral tissues both in animals and in humans (Stein (1993), ibid.). It was further noted that the peripheral opioid effects were more pronounced in inflamed than in non-inflamed tissues.

An anecdotal preliminary study reported an attempt to transdermally locally administer 1–3 mg of morphine to the backs of patients who had undergone failed back operations, primarily using mechanical methods of enhancing skin penetration and absorption of the morphine (ultrasound, massage, heat) as well as by the use of the occlusive topical vehicle Aquaphor (F. Tennant et al., Topical morphine for peripheral pain. Lancet 342:1047–1048 (1993)). Some improvement in pain relief was noted, and the authors speculated that it was due to binding of the morphine to peripheral opioid receptors in inflamed (presumably myofascial) tissue directly under the skin to which the morphine was applied, and absence of morphine in the systemic circulation was claimed. This result is scientifically questionable, however, based on the data of the present invention: there had to be sufficient transdermal transport to carry the morphine completely through the skin and into the underlying inflamed myofascial tissues, which would almost certainly result in a detectible amount of morphine being carried in the systemic circulation. Alternatively, it is possible that the pain relief noted was not reproducible. It is notable that no further reports of this type of administration have been reported since, either by that group or any others.

Severe pain caused or accompanied by inflammation in skin is a particularly intractable problem, because the underlying reasons for it tend to be both long-term and yet not inherently life-threatening, e.g., shingles and various kinds of burns, both of militate against the chronic systemic use of opioid agents. This led to initial investigations into whether it might be possible to be able to induce effective opioid analgesia in such cases without negative systemic opioid administration effects.

Initially, it was thought that it would be necessary to inject the morphine into an inflamed area since the inflammation activates the opioid receptors and it was also believed that the morphine had to be in an enclosed space to stay in contact with the area that was inflamed. The initial experiments were conducted in conjunction with arthroscopic surgery of the knee and a number of patients were medicated after arthroscopic surgery with injected morphine. These patients were medicated either with morphine alone, with a local anesthetic such as Marcaine or a combination of Marcaine and 1 mg of morphine. It was shown that patients receiving morphine into the joint had significantly more pain relief than patients receiving the same dose intravenously (demonstrating a local effect) and that this effect was mediated by intraarticular opioid receptors. Furthermore, patients who received just Marcaine after the surgery had relief but the relief typically did not extend beyond 12 hours or at most the next day after surgery. The patients who received Marcaine plus one mg of morphine in the knee had much better relief extending for at least twice as long as those that received Marcaine alone. See Stein et al. (1991).

At this point, it was still thought that it was necessary to keep the morphine in a closed space, such as in a knee, and the results of such controlled clinical studies reporting analgesia produced by morphine injected into the knee joint were reported in Stein et al., N. Engl. J. Med., 325: 1123–1126 (1991); Comment in N. Engl. J. Med., 325:1168–1169 (1991) and Khoury et al., Anesthes. 77:263–266 (1992). These studies have been replicated by several other groups throughout the world, but this application of morphine was relatively restricted to the practice of orthopedic surgeons using the morphine injected into a joint after arthroscopic surgery and further progress was restricted because it was thought that the morphine had to be contained in the closed space so as to keep the medication in close contact with the inflamed area.

Thus, there was a body of studies determining that opioid receptors were found in various peripheral tissues and suggesting that peripheral opioid effects would be more pronounced in inflamed than in non-inflamed tissues; however, there was no specific determination of how to provide an analgesic effect, using narcotics such as morphine, other than by injection of morphine into a closed space such as a joint. None of these reports discussed the possibility that pain relief could be topically induced in skin, whether inflamed or not, nor was it even known whether peripheral opioid receptors are present in human skin.

Nevertheless, while the need for adequate treatment and relief of pain in inflamed skin was evident, there was a lack of evidence that human skin contained peripheral opioid receptors, and there was doubt whether topical administration in the absence of the enclosed conditions akin to administration into the intra-articular space would work. Thus, the inventors of U.S. Pat. No. 5,589,480 conceived and developed a method of carrying out the concept of effecting topical local analgesia in inflamed skin with opioid agents.

The fact that the opioid effects are more pronounced in inflamed than in non-inflamed tissues is a considerable advantage considering that most painful conditions are associated with inflammation, for example, cancer, arthritis, trauma, post-operative pain, skin lesions, etc. The work disclosed in U.S. Pat. No 5,589,480 demonstrated that extremely small systemically inactive doses of both conventional opioid drugs such as morphine, as well as other opioid agents, can produce potent analgesic effects after local application to inflamed skin in peripheral tissue. U.S. Pat. No. 5,589,480 discloses a method and preparation for a topical application of an opioid drug, such as morphine, for a direct activation of the peripheral opioid receptors on the surface of inflamed skin, without any substantial transdermal or transmucosal systemic delivery of the opioid.

Without wishing to be bound by theory, it is believed that the inflammatory process in peripheral tissue is associated with an increase in sensitivity to the antinociceptive effects of opioid agents, perhaps by activation of opioid receptors located on primary afferent neurons. This may occur by one or more means, e.g., de novo synthesis of opioid receptors which increases the number of receptors; axonal transport of pre-existing receptors to peripheral nerve terminals increasing their concentration and thus sensitivity; some other means of activation of pre-existing neuronal opioid receptors by the inflammatory process. See, e.g., Stein, C., Peripheral and non-neuronal opioid effects. Curr. Opin. Anaesth. 7:347–351 (1994). In addition, again without wishing to be bound by theory, inflamed skin is generally more permeable to topically-administered agents, because the inflammatory process destroys Schwann cells in the epidermis, leading to further exposure of the nerve terminals; inflammation also causes edema, which results in loss of integrity of the epidermis, making the nerve terminals more accessible to topical agents.

Although U.S. Pat. No. 5,589,480 demonstrated the effectiveness of topically-applied opioid analgesics without systemic delivery in inflamed skin, the treatment of peripheral pain in the case of non-inflamed skin faced the additional hurdles of lesser skin permeability, which thus required the addition of skin penetration enhancers and thus risked unwanted systemic delivery, and also did not have the same basis for expecting a successful outcome, i.e., that the inflammatory process in peripheral tissue is associated with an increase in sensitivity to the antinociceptive effects of opioid agents, e.g., due to an increase in the number and/or sensitivity of opioid receptors at peripheral nerve terminals induced by the inflammatory process. Therefore, it could not be predicted whether or how topical analgesia could be induced in non-inflamed skin or mucosa, at least without effecting systemic transdermal or transmucosal delivery as well. Moreover, it was desired to improve, if possible, the effectiveness of topical opioid analgesia induced in inflamed skin or mucosal tissue, without effecting syste-mic delivery of the opioid agents.

As expected, application of the pharmaceutical preparations in accordance with those disclosed in U.S. Pat. No. 5,589,480, which comprised, e.g., morphine sulfate in a simple pharmaceutically acceptable topical excipient, e.g., water, saline or hydrophilic gel such as KY Jelly, when applied to intact, non-inflamed skin in a patient suffering from non-inflammatory skin pain such as peripheral neuropathy, did not work. However, when skin-specific penetration enhancers are added to the topical formulation, it was found that even pain arising in non-inflamed skin could be successfully treated with topical, local analgesic agents which affect peripheral muscarinic receptors in the absence of delivery of clinically effective central nervous system levels. Moreover, these skin penetration enhancers were surprisingly shown to improve the effectiveness of local opioid analgesic agents which bind to opioid receptors in the treatment of pain in inflamed skin or mucosal tissue without the concomitant delivery of substantial amounts of the analgesic agent into the systemic circulation. This invention is fully disclosed in U.S. Ser. No. 09/028,117. The analgesic effect was thus potentiated by topically administering to a patient in need of such treatment a topically effective amount of an analgesic agent, which amount is systemically ineffective for induction of analgesia, admixed with a skin- or mucosa-specific penetration enhancer, such as, e.g., lecithin, and a pharmaceutically acceptable excipient for topical administration, preferably whereby effective analgesia in the non-inflamed skin or mucosal tissue is induced in the substantial absence of transdermal or transmucosal delivery of the opioid analgesic agent to the systemic circulation.

Peripheral Muscarinic Analgesia

L. C. Yang et al., Anesthesiology 88: 334–339 (1998) discloses inducing postoperative analgesia by intra-articular administration of neostigmine in patients undergoing knee arthroscopy, using a counterpart of the method disclosed in Stein et al. (1991). Neostigmine is an acetylcholinesterase inhibitor; it was postulated to induce analgesia by a variety of pathways, presumably via induction of peripheral cholinerigic antinociception by elevating endogenous acetylcholine available to peripheral muscarinic receptors. Systemic administration of neostigmine through the spinal or epidural route of administration has been shown to have dose-related side effects similar to opioids, such as nasuea, vomiting and pruritus.

It would be therefore desirable to provide an additional analgesic in the pharmaceutical arsenal of antinociceptives, by providing an effective topical method of treating pain via the muscarinic receptor pathway of analgesia, without the negative effects of systemic neostigmine administration.

SUMMARY OF THE INVENTION

This invention provides a method of inducing analgesia in intact, inflamed or non-inflamed skin or mucosal tissue, comprising topically administering to a patient in need of such treatment a topically effective amount of an analgesic agent which affects peripheral muscarinic receptors, which amount is systemically ineffective for induction of analgesia, optionally admixed with a skin- or mucosa-specific penetration enhancer, e.g., lecithin, and a pharmaceutically acceptable excipient for topical administration, preferably whereby effective analgesia in the inflamed or non-inflamed skin or mucosal tissue is induced in the substantial absence of transdermal or transmucosal delivery of the analgesic agent to the central nervous system.

A further object of the invention is to provide a pharmaceutical composition comprising an admixture of an analgesic agent which affects peripheral muscarinic receptors, and optionally, a skin- or mucosa-specific penetration enhancer, e.g., lecithin, and a pharmaceutically acceptable excipient for topical administration to inflamed or non-inflamed skin or mucosal tissue, wherein a unit dosage amount of the admixture contains a systemically ineffective amount of the analgesic agent and, optionally, an effective amount of a skin-specific penetration enhancer, such as, e.g., lecithin, and neither the optional skin-specific penetration enhancer nor the excipient substantially enhances transdermal or transmucosal transmission of the analgesic agent into the central nervous system, with the proviso that, when the admixture is a liquid, it further comprises a component that is pharmaceutically unacceptable for parenteral administration.

A still further object of the invention is to provide a pharmaceutical composition comprising an admixture of an analgesic agent which affects peripheral muscarinic receptors, a skin-specific penetration enhancer, such as, e.g., lecithin, and a pharmaceutically acceptable excipient for topical administration to inflamed skin or mucosal tissue, wherein a unit dosage amount of the admixture contains a systemically ineffective amount of the analgesic agent and, optionally, an effective amount of a skin- or mucosa-specific penetration enhancer, such as, e.g., lecithin, and neither the optional skin- or mucosa-specific penetration enhancer nor the excipient substantially enhances transdermal or transmucosal transmission of the analgesic agent into the central nervous system, with the proviso that, when the admixture is a liquid, it further comprises a component that is pharmaceutically unacceptable for parenteral administration.

Upon further study of the specification and claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 illustrates a method and apparatus of the present invention and specifically shows a patient 10 receiving a topical application of an analgesic agent which affects muscarinic receptors, such as neostigmine, optionally admixed with a skin penetration enhancer, using a spray 12. In particular, a small quantity of the neo-stigmine solution is then sprayed onto a painful area 14 on a patient 10 to provide the particular pain relief described above.

As a specific example, 2 mg of neostigmine and 2700 mg of lecithin may be diluted in 120 cc of saline to form the spray 12. The neostigmine/lecithin is initially provided as a solution of 16.8 mg/cc mg/cc, whereby the final spray solution contains 2 mg in a total of 120 cc. Thus, the final concentration of neostigmine in the spray is 0.0168 mg/cc. The specific application may result in approximately 0.1 mg of neostigmine in solution to cover approximately a 6×6 square inch area.

FIG. 2 illustrates the same patient 10 with a painful area 14 with an analgesic agent which affects muscarinic receptors, such as neostigmine, optionally admixed with lecithin, and applied topically in either a gel or a cream.

As a specific example, 2 mg of neostigmine and 2700 mg of lecithin may be mixed with 120 cc of a topical gel. Again the neostigmine/lecithin is initially provided in solution as 0.0168 mg/cc and with the resultant mixture 16 comprising 2 mg of neostigmine in a total of 120 cc. The resultant set or cream is applied to the painful area 14 whereby 0.1 mg of neostigmine covers an area of approximately 6×6 square inches.

DETAILED DESCRIPTION OF THE INVENTION

Surprisingly, it has been found that, analogously to the topical effectiveness of opioid analgesic agents disclosed in U.S. Pat. No 5,589,480, topical application to skin and mucosal tissue of local analgesic agents which bind to muscarinic receptors is effective in treating pain in a patient suffering from inflammatory pain, in the absence of delivery of clinically effective central nervous system levels. These muscarinic receptor effects, which are more pronounced in inflamed than in non-inflamed tissues, are a considerable advantage considering that most painful conditions are associated with inflammation, for example, cancer, arthritis, trauma, post-operative pain, skin lesions, etc. The work disclosed in U.S. Pat. No 5,589,480 demonstrated that extremely small systemically inactive doses of both conventional opioid drugs such as morphine, as well as other opioid agents, can produce potent analgesic effects after local application to inflamed skin in peripheral tissue. Unexpectedly, similar effects are found for topical treatment of inflammatory pain with analgesic agents which bind to muscarinic receptors as well.

Also surprisingly, similarly to the results found for opioid analgesic agents, application of analgesic agents which bind to muscarinic receptors in intact, non-inflamed skin in a patient suffering from non-inflammatory skin pain such as peripheral neuropathy is potentiated by the use of skin-specific penetration enhancers, which are added to the topical formulation, whereby even pain arising in non-inflamed skin can be successfully treated with topical, local analgesic agents which affect peripheral muscarinic receptors in the absence of delivery of clinically effective central nervous system levels. Moreover, these skin penetration enhancers surprisingly improve the effectiveness of local analgesic agents which affects peripheral muscarinic receptors in the treatment of pain in inflamed skin or mucosal tissue without the concomitant delivery of substantial amounts of the analgesic agent into the central nervous system. The analgesic effect is thus potentiated by topically administering to a patient in need of such treatment a topically effective amount an analgesic agent, which amount is systemically ineffective for induction analgesia, admixed with a skin- or mucosa-specific penetration enhancer, such as, e.g., lecithin, and a pharmaceutically acceptable excipient for topical administration, preferably whereby effective analgesia in the inflamed or, in particular, non-inflamed, skin or mucosal tissue is induced in the substantial absence of transdermal or transmucosal delivery of an effective amount of the analgesic agent to the central nervous system.

By "a skin-specific penetration enhancer" is meant an agent which enhances the penetration of an analgesic agent which affects peripheral muscarinic receptors through the uppermost layers of non-inflamed skin to the skin layers in which the peripheral nerves are located that are involved in the painful condition, e.g., inflammatory conditions such as burns, herpetic lesions, acne, as well as peripheral nerves that are indirectly involved in the painful conditions, e.g., wherein an inflammatory disease or condition causes inflammation and pain in the surrounding dermal tissues, e.g., muscle injuries, fractures, arthritis, etc.; as well as non-inflammatory conditions such as diabetic peripheral neuropathy or post-herpetic neuralgia; without substantial transmission or delivery to the CNS. In some cases, the skin-specificity of the penetration enhancer will be determined by its concentration; e.g., at a concentration of 22%, lecithin has been shown to be an excellent vehicle for enhancing transdermal delivery to the systemic circulation, whereas it has been shown that at a concentration of 3–6% in non-inflamed skin, lecithin potentiates the passage of analgesics, e.g., morphine sulfate, across the epidermis into the dermis, yet very little, if any, of the active agent is carried beyond those two layers into the bloodstream. Similarly, at concentrations of 3–6%, lecithin can enhance transport of morphine sulfate across the epidermis and into the dermis in inflamed skin, without transport of substantial amounts into the systemic circulation. Similar optimization can be routinely determined by the skilled worker for analgesic agents which affect peripheral muscarinic receptors, e.g., a concentration of 3–6% lecithin for enhancing transport of neostigmine across the epidermis and into the dermis without transport of substantial amounts into the CNS.

The invention has been tested on a number of patients, and the results are set forth in the Examples. In particular, patients for whom various types of non-inflamed skin conditions, both acute and chronic, were causing intense pain which was not sufficiently alleviated by systemic administration of opioids were treated topically with various formulations of neostigmine, even without skin penetration enhancers.

The results were accomplished with the use of only 0.05 or 0.1 mg of the analgesic agent which affects peripheral muscarinic receptors, such as neostigmine, diluted to be sprayed or applied to a relatively large area of skin such as six inches square and without any side effects such as nausea, vomiting or itching. All of this was accomplished without any significant absorption of the neostigmine into the CNS, since the neostigmine was merely applied topically to the skin or mucous membranes alone, or with a transdermal or transmucosal penetration enhancing agent effective only to substantially transmit the neostigmine into, rather than through, the skin or mucosa.

In addition to the topical application of the analgesic agent which affects peripheral muscarinic receptors, e.g., neostigmine, using a spray, the agent may be applied using a variety of different topical formulations such as gels, creams, etc. Depending upon the particular type of inflammatory or non-inflammatory skin lesion, the topical application will reduce pain in lesions such as diabetic neuralgia and post-herpetic neuralgia, e.g., after herpes zoster (shingles) flare-ups. Other types of pain treatable by the methods and compositions disclosed herein include pain associated with damage to peripheral nerves resulting from chemotherapy treatment for a variety of diseases, including cancer and AIDS. For example, Vincristine chemotherapy can result in peripheral neuropathy not associated with an inflammatory process. The main advantage of the method and pharmaceutical preparations disclosed herein is the excellent pain relief without the typical side effects associated with systemically-effective amounts of oral or injectable drugs which function in the central nervous system. The potential for the present invention is widespread and the topical application opens up a whole new use of muscarinic receptor-active agents without the prior associated problems.

In both methods of application as shown in FIGS. 1 and 2 the relief is substantial and with continued application on a periodic basis to continue this relief without any of the typical side effects such as nausea, vomiting and itching which would typically result if neostigmine were received by the brain. The quantities of the applied analgesic agent described above are illustrative only and it is to be appreciated that lesser and greater quantities may be used, which can be routinely optimized by the skilled worker. In general, amounts analgesically equivalent to 0.05 to 0.1 mg of neostigmine applied to an area of 6 $in^2$, or 0.005 mg/kg of body weight, are preferred. However, the quantity of analgesic agent used in the topical application of the present invention is typically a small fraction of the typical dosage used in other methods of treatment using these agents, e.g., intravenous administration for the reversal of muscle relaxant, e.g., curare, paralysis during surgery.

Analgesic Agents

It is to be appreciated that all the present invention has been described primarily with reference to the use of neostigmine. Other analgesic drugs may be used to interact with the peripheral muscarinic receptors which are present in peripheral tissues in various areas of the body and the invention is not to be limited specifically to neostigmine.

Suitable analgesic agents include compounds which have an analgesic effect through binding to any muscarinic receptor, whereby antinociceptive properties of the agent are functional at the site of pain, as well as agents which enhance the anti-nociceptive properties of other agents which bind to muscarinic receptors. These include, e.g., the muscarinic receptor agonists (e.g., acetylcholine and synthetic choline esters, and cholinomimetic alkaloids, e.g., pilocarpine, muscarine, and arecoline and their synthetic congeners), and the anticholinesterase agents disclosed in chapters 7 and 8 of Goodman and Gilman, The Pharmacological Basis of Therapeutics, 9$^{th}$ ed., McGraw Hill, New York (1996), in particular, neostigmine.

In addition, the analgesic agents present invention can be used in conjunction with topically applied opioid analgesic agents, e.g., in accordance with the invention described in U.S. Pat. No. 5,589,480. Examples of such analgesic agents include, but are not limited to morphine, cyclazocine, piperidine, piperazine, pyrrolidine, morphiceptin, meperidine, trifluadom, benzeneacetamine, diacylacetamide, benzomorphan, alkaloids, peptides, phenantrene and pharmaceutically acceptable salts, prodrugs or derivatives thereof. Specific examples of compounds contemplated by as suitable in the present invention include, but are not limited to morphine, heroin, hydromorphone, oxymorphone, levophanol, methadone, meperidine, fentanyl, codeine, hydrocodone, oxycodone, propoxyphene, buprenorphine, butorphanol, pentazocine and nalbuphine. As used herein, "pharmaceutically acceptable salts, prodrugs and derivatives" refers to derivatives of the opioid analgesic compounds that are modified by, e.g., making acid or base salts thereof, or by modifying functional groups present on the compounds in such a way that the modifications are cleaved, either in routine manipulation or in vivo, to produce the analgesically active parent compound. Examples include but are not limited to mineral or organic salts of acidic residues such as amines, alkali or organic salts of acidic residues such as carboxylic acids, acetate, formate, sulfate, tartrate and benzoate derivatives, etc. Suitable opioid analgesic agents, including those specifically mentioned above, are also described in Goodman and Gilman, ibid, chapter 28, pp. 521–555.

In addition, other active agents may be included in the pharmaceutical composition, e.g., topically-effective anaesthetics such as xylocaine, cocaine, lidocaine, benzocaine, etc., which may provide a more immediate, if less effective in the long run, level of pain relief until the analgesic agent becomes fully effective. Other active agents which may be present in the pharmaceutical preparations include, e.g., antibiotics, and especially those agents which themselves cause pain when applied to the inflamed site due to their inherent properties, e.g., pH.

Still other agents can also be administered, preferably topically, to potentiate the effects of the topically-administered analgesic agents. For example, dextromethorphan, a non-addictive opioid compound, can be co-administered, preferably topically, although parenteral administration is also effective, to enhance the effectiveness of the topically administered analgesic agent. Without wishing to be bound by theory, it is believed that dextromethorphan has previously unappreciated analgesic properties in peripheral nerves. Suitable concentrations of dextromethorphan are routinely ascertainable by the skilled worker, and include the normal therapeutic amounts administered parenterally for conventional purposes, e.g., as a cough suppressant, or less, and routinely determinable amounts for topical administration; for example, 1 g of dextromethorphan can be added to a composition of Example 1 to provide additional relief from pain.

Transdermal Enhancers

The most important criterion for selecting a suitable topical excipient is that, while it enhances percutaneous delivery of the analgesic agent into the skin or mucous membrane, it does not enhance delivery of the analgesic agent through the skin or mucosa into the systemic circulation, e.g., it does not provide substantial transdermal or transmucosal transmission, and more particularly does not provide transmission to the central nervous system. In the case of some enhancers, the amount and rate of transmission and thus the difference between providing transdermal or transmucosal delivery and not doing so will lie in the selection of the amount of enhancer used, the intactness of the skin, the type of skin or mucosal tissue which is being treated, the nature of the analgesic agent, etc. However, these are routinely determinable parameters which can be optimized for a particular condition by one of ordinary skill in the art.

Various methods have been used to increase skin permeation of drugs include penetration enhancers, prodrugs, superfluous vehicles, iontophorosis, phonophoresis and thermophoresis. In particular, penetration enhancers are preferred.

Ideal penetration enhancers have no irritancy or toxicity to the skin, as well as high enhancing effects. Enhancers themselves should be physiochemically stable and not have pharmacologic effects and preferably should not have smell, color or taste.

The stratum corneum provides the principal barrier to the percutaneous penetration of topically applied substances. It is the most superficial, cutaneous layer, the horny layer, which consists of flat, scalelike "squames" made up of the fibrous protein keratin. The squames are continually being replaced from below by epidermal cells that die in the process of manufacturing keratin. It is unlikely that the emulsified fat on the skin surface greatly affects permeability. However, vehicles can control, to a great extent, the rate of penetration of drugs that are applied to the skin. The intercellular lipids may be important for the permeability barrier in skin.

It is known that some combinations of enhancers are synergistic in action, as with ethanol as a vehicle for the potent enhancer laurocapram. Some combinations are not synergistic; for instance, (N) decylmethylsulfoxide lowers the zeta potential of the skin; thus, enhancement due to conduction flow (iontophoresis) is minimized. In any case, optimization of suitable transdermal or transmucosal enhancing preparations for a given use is routine for one of ordinary skill in the art.

Thus, suitable topical transdermal or transmucosal enhancing agents can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87. For example, suitable enhancers for transdermal absorption include ethanol, propylene glycol, water, sodium oleate, leucinic acid, oleic acid, capric acid, sodium caprate, lauric acid, sodium laurate, neodecanoic acid, dodecyl-amine, cetryl lactate, myristyl lactate, lauryl lactate, methyl laurate, phenyl ethanol, hexamethylene lauramide, urea and derivatives, dodecyl N,N-dimethylamino acetate, hydroxyethyl lactamide, phyophatidylcholine, sefsol-318 (a medium chain glyceride), isopropyl myristate, isopropyl palmitate, several surfactants, including polyoxyethylene (10) lauryl ether (Brij 361 R), diethyleneglycol lauryl ether (PEG-2-L), laurocapram (Azone; 1,1-dodecylazacycloheptan-2-one), acetonitrile, 1-decanol, 2-pyrrolidone, N-methylpyrrolidone, N-ethyl-1-pyrrolidone, 1-methyl-2-pyrrolidone, 1-lauryl-2-pyrrolidone, sucrose monooleate, dimethylsulfoxide (DMSO) about 80% concentration required, decylmethylsulfoxide (n) enhances primarily polar or ionic molecules (soluble in ethanol), acetone, polyethylene glycol 100–400 MW, dimethylacetamide, dimethylforamide, dimethylisosorbide, sodium bicarbonate, various $N_{7-16}$-alkanes, mentane, menthone, menthol, terpinene, D-terpinene, dipentene, N-nonalol and limonene.

Without wishing to be bound by theory, the following outline sets forth proposed mechanisms of action of common chemical penetration enhancers:

Sulfoxides (e.g., dimethyl sulfoxide [DMSO], N-decylmethylsulfoxide)

Reduces resistance of the skin to the drug molecule

Promotion of drug partitioning from the dosage form

Elution of lipid, lipoprotein and nucleoprotein structures of the stratum corneum Increase lipid fluidity by disrupting tightly packed lipid chains which results in an interaction between polar head groups of the lipids via hydrogen bonding Protein interactions resulting in a change in protein conformation, thus creating a passage of aqueous channels May increase polar drugs more effectively than nonpolar drugs Alcohols (e.g., ethanol)

Increase solubility of drug in fatty matrix of stratum corneum

Extraction of lipidic and peptidic substances, therefore creating a porous pathway for polar compounds Polyols (e.g., propylene glycol)

Solubilize alpha-keratin and occupy hydrogen bonding sites, thus reducing drug-tissue bonding sites and promoting permeation Fatty Acids (e.g., lauric, myristic, palmitic, stearic)

Disrupt membrane lipid packing by selective perturbation of the intercellular lipid bilayers present in the stratum corneum Esters (e.g., isopropyl palmitate, isopropyl myristate)

Increase lipid fluidity by forming a salvation shell around polar head groups which leads to a disruption of lipid packing Permeation into liposomal bilayers, thus increasing fluidity and promoting permeation of drug molecules Increasing diffusivity of the stratum corneum and the partition coefficient between the stratem corneum and vehicle of both drug and solvent Amides (e.g, urea)

Increase moisture of the skin

Act as a mild keratolytic through an ability to split hydrogen bonds between cells in the stratum corneum Surface-Active Agents (e.g., Pluronic F127, sodium lauryl sulfate, lecithin, docusate sodium, polysorbates)

Absorb at interfaces and interact with biological membrane

Removal of water-soluble agents that normally act as plasticizers

Emulsify sebum, thereby enhancing the thermodynamic activity coefficients of drugs Extraction of lipids from the stratum corneum Penetration of surfactant into the intercellular lipid matrix of the cornfield layer Water (occlusion)

Cause swelling of the corneocytes

Increase the amount of water associated with the intercellular lipid domain

Increase the temperature

Increase lipid fluidity and disorder

May induce lipid phase separation by altering the equilibrium interaction between water and intercellular lipid domains Prevent evaporation of transpirational moisture Topical Excipients The choice of topical excipient as a vehicle for the analgesic agent, while routine, is an important aspect of the claimed invention. The most important criterion for selecting a suitable topical excipient is that it does not enhance delivery of the analgesic agent to the systemic circulation or to the central nervous system by substantial transdermal or transmucosal transmission. For example, in general, it is preferred that the topical excipient not have substantial occlusive properties, which enhance percutaneous transmission of the analgesic agent through the skin or mucosa into the systemic circulation. Such occlusive vehicles include hydrocarbon bases such as white petrolatum (e.g., Vaseline); anhydrous absorption bases such as hydrophilic petrolatum and anhydrous lanolin (e.g., Aquaphor); and water-in-oil emulsion bases such as lanolin and cold cream.

More preferred are vehicles which are substantially nonocclusive, and generally include those which are water-soluble, such as oil-in-water emulsion bases (creams or hydrophilic ointments) and water-soluble bases such as polyethylene glycol-based vehicles and aqueous solutions gelled with various agents such as methylcellulose, hydroxyethyl cellulose, and hydroxypropyl methylcellulose (e.g., K-Y Gel).

Suitable topical excipients and vehicles can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87.

Other additives, e.g., for enhancing the adherent properties of the pharmaceutical preparation to various special skin areas, e.g., the axillar, plantar and palmar skin, and mucosal tissues, e.g., in the mouth, on the throat, on the genitalia, particularly the external female genitalia, can be similarly routinely selected and the preparation adapted to such use by one of ordinary skill in the art.

Other Definitions

By "mucosal tissue" is meant tissue comprising a superficial epithelial membrane which is lubricated by mucus. This includes, inter alia, the lining of the mouth, throat, nose, tympanic membrane, external female genitalia, vagina, urethra, rectum and anus. It does not include the conjunctiva of the eye.

By "directly activate peripheral muscarinic receptors in the skin or mucosal tissue, but not sufficient to activate central nervous system muscarinic receptors" is meant that the analgesic action of the analgesic agent is mediated through interaction with peripheral muscarinic receptors, e.g., and not through interaction with CNS receptors. See, e.g., Stein (1993), supra, which sets forth criteria for evaluating peripheral opioid receptor antinociception, as an example for such evaluation.

By "substantial absence of" or "does not enhance" transdermal or transmucosal delivery of the analgesic agent is meant that upon the induction of analgesia, less than 25%, preferably less than 10%, more preferably less than 5%, still more preferably 1% and most preferably none of the analgesic agent has passed through the stratum corneum into the systemic circulation. In particular, an insufficient amount for induction of systemic analgesia is delivered to the systemic circulation.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the foregoing and in the following examples, all temperatures are set forth uncorrected in degrees Celsius; and, unless otherwise indicated, all parts and percentages are by weight.

The entire disclosures of all applications, patents and publications, cited above and below, including U.S. Ser. No. 08/291,614, filed Aug. 17, 1994, now U.S. Pat. No. 5,589,480, and U.S. Ser. No. PCT/96/19618, filed Dec. 12, 1996, as well as U.S. Ser. No. 09/028,117, filed Jan. 23, 1998, are hereby incorporated by reference.

EXAMPLES

Example 1

Acute Herpes

The patient is a 71 year old female with a history of acute herpes attack. The lesion was at the level of the cervical area in the back of the neck and encompassing the back of the head and the neck. The patient was treated with anti-viral medications, with Vicodin (hydrocodone) with Motrin, without any relief of the pain. The patient was unable to sleep because every time she turned in bed, the back of her head touched the pillow and the Patient woke up. The patient was then given topical neostigmine as a mixture of 500 mcg of neostigmine in 30 cc of K-Y Gel.

On follow-up, the patient stated that she had significant relief of her pain, and to her amazement, after she put it on at night, she woke up the next morning with the back of her head on the pillow, which usually wakes her up in pain, and that she did not have any pain while she was resting with the back of her head on the pillow. She did not need to take any other oral pain medication, and she was very satisfied with the relief.

Example 2

Cold Sores in the Mouth

The patient is a 31-year-old female with painful cold sores in the mouth, and she had been treated with the usual anti-viral medication without much relief. The patient was offered with topical 30 cc of K-Y Gel with 500 mcg of neostigmine which was used in an amount to cover the area of irritation. The patient stated that within 15 min. The pain was less, and that by the next day she had full relief of her pain. She only had to use it about three times that day.

Example 3

Gout

The patient is a 71-year-old male with a history of gout. He was referred to the pain clinic because of acute exacerbation of the gout in his big toe, and the patient was unable to control his pain with the usual oral pain medication he had been receiving and the gout medication he was taking. The patient was provided with 30 cc of K-Y Gel with 500 mcg of neostigmine, and directed to cover the area of pain with the medication, and to repeat every three to four hours as needed. The patient stated that by the next morning his pain was fully gone, and he did not need any of the other pain medications.

Example 4

Broken Wrist

The patient is a 70-year-old male with a broken wrist, who was complaining of severe pain with swelling and redness of the wrist. The patient was being taken to the operating room for closed reduction of the fracture. The patient was supplied with 500 mcg neostigmine in 30 cc K-Y Gel and directed to apply the mixture to his wrist himself, so he did not hurt from the application. Within 10 minutes, the patient started feeling a difference in his pain and was able to mobilized his hand better than before, and within the next half hour the patient had no pain at all. The arm was immobilized, and he had some pain on mobilization of the wrist.

Example 5

Fractured Clavicle

The patient is a 58-year-old gentleman with a fractured clavicle, painful with breathing, and not responsive to the oral anti-inflammatory he was taking. The patient was given 30 cc of K-Y Gel, 500 mcg of neostigmine, and was direct to apply it over his clavicle every three to four hours. After four hours, the patient called back stating that his pain started to disappear within the half hour and within the hour after the application the pain was significantly less than before, and he was very excited about it as he was able to stop all his anti-inflammatory medications, which were causing him a lot of gastrointestinal side-effects.

Example 6

Sprained Ankle

A 45-year-old gentleman with a sprained ankle, who was in severe pain, unresponsive to the oral anti-inflammatory he was receiving, and the hot and cold packs applied to his ankle. The patient was provided with 30 cc of K-Y Gel and 500 mcg of neostigmine, and was directed to use it every three to four hours. After a half hour of using it, the pain started subsiding, and after three applications, the patient was definitely in significantly less pain than before. The patient was excited about this, as it was providing him with much more relief than the other treatment he had received thus far.

Example 7

Second Degree Burn

The patient is a 50-year-old-female with severe pain in her hand, resulting from a second degree burn of her hand. The patient has blisters and was unable to mobilize the fingers because of pain. She was provided with 30 cc of K-Y Gel and 500 mcg of neostigmine, and was directed to use it every three to four hours. The patient applied the cream on her burn, and within 10–15 mins the patient started seeing a change in the quality of her pain, and within the next few hours, the pain had significantly subsided.

Example 7

Composition

A. An exemplary composition according to the invention comprises:

Neostigmine: 500 mcg

K-Y Gel: 30 cc

B. A second exemplary composition according to the invention comprises:

Neostigmine: 500 mcg

Polyethylene glycol: to wet

Soya lecithin: 2700 mg (4.5 ml)

White petrolatum: 84 g

Dextromethorphan: 1 g

Pluronic 30% 30 ml

Example 8

Severe Knee Pain

The patient is a 58 year old gentleman with severe pain in his knee. He underwent arthroscopic surgery of the knee, but the pain stayed the same. The patient was referred for further treatment and the patient was given topical neostigmine to apply on his knee on his follow-up visit, and he was provided with 120 cc of K-Y jelly with 2 mg of neostigmine mixed together. The patient was instructed to cover the area of pain every three to four hours. The patient was using approximately 2 to 3 cc of the mixture and was applying the mixture every three to four hours. At the follow-up visit, the patient stated that he had excellent relief of his pain which was lasting for close to three to four hours. The patient states that because of the use of this cream, he did not need to use any further oral medication to control his pain. He even stopped his anti-inflammatories.

Example 9

Severe Shingles of The Chest

The patient is an 81 year old female with severe shingles on her chest. She has used oral narcotics and antiviral medication without success. The patient was referred to the clinic about two weeks after the onset of the pain and was complaining of severe pain unrelieved with any kind of treatment. The patient was given 120 cc of K-Y jelly with 2 mg of neostigmine mixed together and instructed to use enough to cover the area of pain and to repeat it every three to four hours if needed. The next day the patient called stating that it is the best relief that she ever had, that the pain had gone away and she does not need to use any other sort of pain medication and she uses close to 4 to 5 cc to cover all the area of her chest and her arm. She reported no side effects.

Example 10

Severe Low Back Pain

The patient is a 45 year old female with severe low back pain. She had two back surgeries to relieve her pain without success. She was maintained on oral narcotics and she was using approximately 10 tablets of pain medication daily. The patient was contemplating undergoing a third surgery to control her pain. The patient was provided with 120 cc of K-Y jelly with 2 mg of neostigmine to be applied every three to four hours as needed. On her first follow-up visit, the patient stated it was the best relief she ever had. She stated that the pain goes away within five to ten minutes after applying the topical neostigmine and said the relief will last three to four hours. Her intake of pain medications dropped by almost half, and now she is contemplating not undergoing any further surgery because of the pain relief she is getting with the cream.

Example 11

Arthritis of The Hands

A 43 year old female with arthritis of the hands was unable to extend her fingers because of pain. The patient was supplied with 120 cc of K-Y jelly with 2 mg of neostigmine and was instructed to use it every three to four hours as needed. The patient stated that she used about 2–3 cc per treatment which was enough to cover her hand and fingers and after using it, within a few minutes, she was able to extend her hands fully and the pain had completely disappeared.

Example 12

A Horse With Severe Back Pain

The horse was unresponsive to the usual anti-inflammatories. Because of pain, the horse was unable to be saddled and because of his pain, he would be unable to make any turns or twists. The horse trainer was provided with 120 cc of K-Y jelly with 2 mg of neostigmine and started to use it every three to four hours. Ten minutes after using it the first time, the horse was walking as if nothing were wrong with him and was able to be saddled and taken on a ride for a couple of hours.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of inducing analgesia in inflamed or non-inflamed skin or mucosal tissue, comprising topically administering to a patient in need of such treatment a topically effective amount of an analgesic agent which affects peripheral muscarinic receptors, which amount is systemically ineffective for induction of analgesia, optionally admixed with a skin- or mucosal-specific penetration enhancer and a pharmaceutically acceptable excipient for topical administration, whereby effective analgesia in the inflamed or non-inflamed skin or mucosal tissue is induced in the substantial absence of transdermal or transmucosal delivery of the analgesic agent to the central nervous system.

2. A method of claim 1, wherein the skin- or mucosal-specific penetration enhancer is present and is lecithin.

3. A method of claim 1, wherein the analgesic agent is administered in an amount analgesically equivalent to 100 mcg of neostigmine per 6 in$^2$ of skin.

4. A method of claim 1, wherein the analgesic agent is neostigmine.

5. A method of claim 1, wherein the excipient is a liquid and the admixture is administered by spraying the liquid onto the skin or mucosal tissue.

6. A method of claim 1, wherein the excipient is a gel or cream and the admixture is administered by spreading the gel or cream on the skin or mucosal tissue.

7. A method of claim 6, wherein the amount administered is analgesically equivalent to 100 mcg of neostigmine.

8. A pharmaceutical composition comprising an admixture of an analgesic agent which affects peripheral muscarinic receptors, a skin- or mucosal-specific penetration enhancer and a pharmaceutically acceptable excipient for topical administration to inflamed or non-inflamed skin or mucosal tissue, wherein a unit dosage amount of the admixture contains a systemically ineffective amount of the analgesic agent, and the amount of penetration enhancer is effective to enhance penetration of the analgesic agent into the skin or mucosal tissue, and the penetration enhancer and excipient do not enhance transdermal or transmucosal transmission of the analgesic agent to the central nervous system, with the proviso that, when the admixture is a liquid, it further comprises a component that is pharmaceutically unacceptable for parenteral administration.

9. A pharmaceutical composition of claim 8, wherein a unit dosage amount of the analgesic agent is analgesically equivalent to 100 mcg of neostigmine per 6 in$^2$ of skin.

10. A pharmaceutical composition of claim 8, wherein the analgesic agent is neostigmine.

11. A pharmaceutical composition of claim 8, wherein the excipient is a liquid and the admixture is administered by spraying the liquid onto the skin or mucosal tissue.

12. A pharmaceutical composition of claim 8, wherein the excipient is a gel or cream and the admixture is administered by spreading the gel or cream on the skin or mucosal tissue.

13. A pharmaceutical composition of claim 8, in a unit dosage form analgesically equivalent to 50–100 mcg of neostigmine.

14. A pharmaceutical composition comprising an admixture of an analgesic agent which affects peripheral muscarinic receptors, optionally a skin- or mucosal-penetration enhancer and a pharmaceutically acceptable excipient for topical administration, wherein the enhancer and the excipient do not substantially enhance transdermal or transmucosal transmission of the analgesic agent to the central nervous system, in a unit dosage form analgesically equivalent to 50–100 mcg of neostigmine.

15. A container adapted for spraying a measured amount of a liquid onto skin, and containing a pharmaceutical composition comprising an admixture of an analgesic agent which affects peripheral muscarinic receptors, optionally a skin- or mucosal-penetration enhancer and a pharmaceutically acceptable excipient for topical administration.

16. A method of inducing analgesia in inflamed or non-inflamed skin or mucosal tissue, comprising topically administering to a patient in need of such treatment a topically analgesically effective amount of an analgesic agent which affects peripheral muscarinic receptors, optionally admixed with a skin- or mucosal-penetration enhancer and a pharmaceutically acceptable excipient for topical administration, wherein the amount of analgesic agent is sufficient to directly activate peripheral muscarinic receptors in the inflamed or non-inflamed skin or mucosal tissue, but not sufficient to activate central nervous system muscarinic receptors.

17. A method of claim 16, whereby effective analgesia in the inflamed or non-inflamed skin or mucosal tissue is induced in the substantial absence of transdermal or transmucosal delivery of the analgesic agent.

18. A method of claim 16, wherein the analgesic agent is administered in an amount analgesically equivalent to 100 mcg of neostigmine per 6 in$^2$ of skin.

19. A pharmaceutical composition of claim 8, wherein the skin- or mucosal-specific penetration enhancer is present and is lecithin.

20. A pharmaceutical composition of claim 14, wherein the skin- or mucosal-specific penetration enhancer is present and is lecithin.

21. A container of claim 15, wherein the skin- or mucosal-specific penetration enhancer is present and is lecithin.

22. A method of claim 16, wherein the skin- or mucosal-specific penetration enhancer is present and is lecithin.

23. A pharmaceutical composition of claim 8, further comprising an effective amount of dextromethorphan.

24. A method of claim 1, further comprising administering an effective amount of dextromethorphan.

25. A method of claim 16, further comprising administering an effective amount of dextromethorphan.

* * * * *